United States Patent
Lu

(10) Patent No.: US 6,697,673 B1
(45) Date of Patent: Feb. 24, 2004

(54) IMPLANTABLE STIMULATION DEVICE AND METHOD FOR DETECTING CAPTURE OF A HEART CHAMBER USING CROSS-CHAMBER CONDUCTED DEPOLARIZATION

(75) Inventor: Richard Lu, Thousand Oaks, CA (US)

(73) Assignee: Pacesetter, Inc., Sylmar, CA (US)

( * ) Notice: Subject to any disclaimer, the term of this patent is extended or adjusted under 35 U.S.C. 154(b) by 224 days.

(21) Appl. No.: 09/952,728

(22) Filed: Sep. 13, 2001

(51) Int. Cl.[7] .............................................. A61N 1/368
(52) U.S. Cl. ....................................................... 607/28
(58) Field of Search ........................................ 607/9, 28

(56) References Cited

U.S. PATENT DOCUMENTS

| | | | |
|---|---|---|---|
| 3,757,792 A | 9/1973 | Mulier et al. | 128/419 P |
| 3,920,024 A | 11/1975 | Bowers | 128/419 PG |
| 3,949,758 A | 4/1976 | Jirak | 128/419 PG |
| 4,055,189 A | 10/1977 | Auerbach et al. | 128/419 PG |
| 4,114,627 A | 9/1978 | Lewyn et al. | 128/419 PT |
| 4,228,803 A | 10/1980 | Rickards | 128/419 PG |
| 4,305,396 A | 12/1981 | Wittkampf et al. | 128/419 PG |
| 4,686,988 A | 8/1987 | Sholder | 128/419 PT |
| 4,708,142 A | 11/1987 | DeCote, Jr. | 128/419 PT |
| 4,955,376 A | 9/1990 | Callaghan et al. | 128/419 PG |
| 4,969,460 A | 11/1990 | Callaghan et al. | 128/419 PG |
| 5,324,310 A | 6/1994 | Greeninger et al. | 607/28 |
| 5,331,966 A | 7/1994 | Bennett et al. | 128/696 |
| 5,350,410 A | 9/1994 | Kleks et al. | 607/28 |
| 5,431,693 A | 7/1995 | Schroeppel | 607/28 |
| 5,782,889 A | 7/1998 | Hognelid et al. | 607/28 |
| 5,800,465 A * | 9/1998 | Thompson et al. | 607/9 |
| 5,902,324 A * | 5/1999 | Thompson et al. | 607/9 |
| 6,128,535 A | 10/2000 | Maarse | 607/28 |
| 6,421,564 B1 * | 7/2002 | Yerich et al. | 607/9 |
| 6,434,428 B1 * | 8/2002 | Sloman et al. | 607/28 |

* cited by examiner

Primary Examiner—Carl Layno

(57) ABSTRACT

An implantable cardiac stimulation device and associated method to verify capture of a stimulated atrial site by detecting a conducted depolarization at another atrial site or in the opposite atrial chamber. A signal received during an atrial capture detection window is compared to a depolarization signal threshold or to a depolarization signal template in order to verify detection of a conducted depolarization signal as evidence of capture at the stimulated site. By sensing depolarization signal away from the stimulated site, the negative effects of lead polarization normally encountered when detecting an evoked response are avoided.

22 Claims, 4 Drawing Sheets

IMPLANTABLE STIMULATION DEVICE AND METHOD FOR DETECTING CAPTURE OF A HEART CHAMBER USING CROSS-CHAMBER CONDUCTED DEPOLARIZATION

CROSS-REFERENCE TO RELATED APPLICATIONS

This application relates to U.S. patent application Ser. No. 09/847,703, filed May 1, 2001, titled "Method and Apparatus for Biventricular Stimulation and Capture Monitoring," which, in turn, claims the priority of U.S. Provisional Application Serial No. 60/204,277, filed May 15, 2000. Both applications are assigned to the same assignee as the present application.

FIELD OF THE INVENTION

The present invention relates to capture verification in a cardiac stimulation device. More specifically, the present invention relates to capture verification in bi-atrial, bi-ventricular, or multi-chamber stimulation devices where capture of a stimulated chamber is verified by detecting a conducted depolarization in the opposing chamber.

BACKGROUND OF THE INVENTION

In the normal human heart, the sinus node, generally located near the junction of the superior vena cava and the right atrium, constitutes the primary natural pacemaker initiating rhythmic electrical excitation of the heart chambers. The cardiac impulse arising from the sinus node is transmitted to the two atrial chambers, causing a depolarization known as a P-wave and the resulting atrial chamber contractions. The excitation pulse is further transmitted to and through the ventricles via the atrioventricular (A-V) node and a ventricular conduction system causing a depolarization known as an R-wave and the resulting ventricular chamber contractions.

Disruption of this natural pacing and conduction system as a result of aging or disease can be successfully treated by artificial cardiac pacing using implantable cardiac pacing devices, including pacemakers and implantable defibrillators, which deliver rhythmic electrical pulses or anti-arrhythmia therapies to the heart at a desired energy and rate. One or more heart chambers may be electrically paced depending on the location and severity of the conduction disorder.

Modern pacemakers and implantable defibrillators possess numerous operating parameters, such as pacing pulse energy, pacing rate, sensing threshold, pacing mode, etc., that must be programmed by the clinician to satisfy individual patient need. In practice, this programming process can be time consuming and complicated. A common goal of pacemaker manufacturers, therefore, is to fully automate pacemaker function in order to minimize the complexity of programming operations and to maximize the safety and effectiveness of the cardiac pacing device.

One function of the pacemaker is to deliver a pacing pulse of sufficient energy to depolarize the cardiac tissue causing a contraction, a condition commonly known as "capture." Automating this function continues to be a strong focus of development efforts by pacemaker manufacturers. One approach to ensure capture is to deliver a fixed high-energy pacing pulse. While this approach, used in early pacemakers, is straightforward, it quickly depletes battery charge and can result in patient discomfort due to extraneous stimulation of surrounding skeletal muscle tissue.

Therefore, the aim commonly strived for in the pacemaker industry is to deliver pacing pulses at or slightly higher than the capture "threshold." Threshold is defined as the lowest stimulation pulse energy at which capture occurs. By stimulating the heart chambers at or just above threshold, comfortable and effective cardiac stimulation is provided without unnecessary depletion of battery charge. Capture threshold, however, is extremely variable from patient-to-patient due to variations in electrode systems used, electrode positioning, physiological and anatomical variations of the heart itself, and so on. Therefore, at the time of device implant, the threshold is determined by a clinician who observes an ECG recording while pulse energy is decreased, either by decrementing the pulse amplitude or the pulse width, until a loss of capture occurs.

Typically, the pulse width is fixed and the pulse amplitude is decremented. The stimulation pulse energy is then programmed to a setting equal to the lowest pulse energy at which capture still occurred (threshold) plus some safety margin to allow for small fluctuations in threshold. Selection of this safety margin, however, can be arbitrary. Too low of a safety margin may result in loss of capture, an undesirable result for the patient. Too high of a safety margin will lead to premature battery depletion and potential patient discomfort.

Furthermore, the threshold will vary over time within a patient as, for example, fibrotic encapsulation of the electrode occurs during the first few weeks after surgery. Fluctuations may even occur over the course of a day or with changes in medical therapy or disease state. Hence, techniques for monitoring the cardiac activity following delivery of a pacing pulse have been incorporated in modem pacemakers in order to verify that capture has indeed occurred. If a loss of capture is detected by such "capture-verification" algorithms, a threshold test is performed by the cardiac stimulation device in order to re-determine the threshold and automatically adjust the stimulation pulse energy. This approach, called "automatic capture", improves the patient's comfort, reduces the necessity of unscheduled visits to the medical practitioner, and greatly increases the pacemaker's battery life by conserving the energy used to generate stimulation pulses.

The most widely implemented technique for determining whether capture has occurred is monitoring the intracardiac electrogram (EGM) received on the implanted cardiac electrodes. Heart activity is monitored by the pacemaker by keeping track of the stimulation pulses delivered to the heart and examining the EGM signals that are manifest concurrent with depolarization or contraction of muscle tissue (myocardial tissue) of the heart. Through sampling and signal processing algorithms, the presence of an "evoked response" following a stimulation pulse is determined. The "evoked response" is the depolarization of the heart tissue in response to a stimulation pulse, in contrast to the "intrinsic response" which is the depolarization of the heart tissue in response to the heart's natural pacing function.

When capture occurs, the evoked response is an intracardiac P-wave or R-wave that indicates contraction of the cardiac tissue in the atria or ventricles, respectively, in response to the applied stimulation pulse. For example, using such an evoked response technique, if a stimulation pulse is applied to the ventricle (hereinafter referred to as a Vpulse), a response which is sensed by ventricular sensing circuits of the pacemaker following the application of the Vpulse and meets the capture detection criteria, is presumed to be an evoked response that evidences capture of the ventricles.

However, for several reasons it would be quite difficult to detect a true evoked response. First, because the evoked response may be obscured by a pacing pulse and therefore difficult to detect and identify. Second, the evoked response may be difficult to distinguish from an intrinsic response since an intrinsic response may occur approximately the same time as an evoked response is expected to occur. Third, the signal sensed by the pacemaker's sensing circuitry immediately following the application of a stimulation pulse may not be a QRS complex but noise, either electrical noise caused, for example, by electromagnetic interference, myopotential noise caused by skeletal muscle contraction, or "cross-talk," defined as signals associated with stimulation pulses or intrinsic events occurring in other heart chambers.

Another signal that interferes with the detection of an evoked response, and potentially the most difficult for which to compensate because it is usually present in varying degrees, is lead polarization. A lead-tissue interface is where an electrode of the pacemaker lead contacts the cardiac tissue. Lead polarization is commonly caused by electrochemical reactions that occur at the lead-tissue interface due to application of an electrical stimulation pulse, such as an atrial pacing pulse, at the interface.

If the evoked response is sensed through the same electrodes through which the stimulation pulses are delivered, the resulting polarization signal, also referred to herein as an "afterpotential", formed at the electrode can corrupt the evoked response that is sensed by the sensing circuits. This undesirable situation occurs often because the polarization signal can be three or more orders of magnitude greater than the evoked response. Furthermore, the lead polarization signal is not easily characterized; it is a complex function of the lead materials, lead geometry, tissue impedance, stimulation energy and other variables, many of which are continually changing overtime.

In each of the above cases, the result may be a false positive detection of an evoked response. Such an error leads to a false capture indication, which in turn leads to missed heartbeats, a highly undesirable and potentially life-threatening situation. Another problem results from a failure by the pacemaker to detect an evoked response that has actually occurred. In that case, a loss of capture is indicated when capture is in fact present, which also constitutes an undesirable situation that could cause the pacemaker to unnecessarily invoke the threshold testing function in a chamber of the heart, and to inappropriately deliver backup pulses.

Automatic threshold testing is only invoked by the pacemaker when loss of atrial or ventricular capture is detected, or a predetermined duration has expired. An exemplary conventional threshold test procedure is performed as follows. When loss of capture is detected, the pacemaker increases the stimulation pulse output level to a relatively high predetermined testing level at which capture is certain to occur, and thereafter decrements the output level until capture is lost. The stimulation energy is then set to a level slightly above the lowest output level at which capture was attained. Thus, capture verification is of utmost importance in proper determination of the pacing threshold.

It would thus be desirable to provide an implantable, multi-chamber cardiac stimulating device in which reliable capture verification is performed. It would also be desirable to provide a system and method for capture verification that avoids the adverse effect of polarization and noise. It would further be desirable to enable the pacemaker to perform capture verification without requiring dedicated circuitry and/or special sensors.

SUMMARY OF THE INVENTION

The present invention addresses these needs by providing an implantable cardiac stimulation device capable of verifying capture in a stimulated chamber by detecting a conducted depolarization in the opposing chamber that has not been stimulated, during a capture detection window. As used herein, conducted depolarization includes an intrinsic depolarization of the opposing chamber in response to the stimulation, or an evoked response signal that has propagated along an inter-atrial path (e.g., atrium to atrium) to the opposing chamber, in response to the stimulation. In a preferred embodiment, a test is performed to confirm inter-chamber conduction, prior to detecting the conducted depolarization.

Thus, for example, if stimulation is delivered in a right atrial chamber, capture of the right atrium is verified by detecting a conducted depolarization in the left atrium. Likewise, if stimulation is delivered in the left atrium, capture is verified by detecting a conducted depolarization in the right atrium.

The foregoing and other features of the present invention are realized by an implantable cardiac stimulation device equipped with cardiac data acquisition capabilities. A preferred embodiment of the stimulation device includes a control system for controlling the operation of the device; a set of leads for receiving cardiac signals and for delivering atrial and ventricular stimulation pulses; a set of sensing circuits comprised of sense amplifiers for sensing and amplifying the cardiac signals; and pulse generators for generating atrial and ventricular stimulation pulses. In addition, the stimulation device includes memory for storing operational parameters for the control system, and for storing data such as depolarization threshold data. The device also includes a telemetry circuit for communicating with an external programmer.

The present invention further presents a method for setting a capture detection window during which a depolarization signal may be detected. This capture detection window is applied to the intracardiac electrogram signal received from sensing electrodes positioned in or near the chamber opposite to the chamber being stimulated. Alternatively, a depolarization signal template may be generated and stored in memory such that a sensed signal from the chamber opposite the stimulated chamber may be compared to the depolarization signal template to determine if capture has occurred in the stimulated chamber.

By sensing the intracardiac electrogram signal in the chamber opposite the stimulated chamber, the negative effects of lead polarization on the electrogram signal sensed in the stimulated cardiac chamber are avoided. Thus the present invention improves cardiac stimulation device performance by providing a method for reliably verifying capture without additional hardware or complex software.

BRIEF DESCRIPTION OF THE DRAWINGS

Further features and advantages of the present invention may be more readily understood by reference to the following description taken in conjunction with the accompanying drawings, in which.

DETAILED DESCRIPTION OF THE PREFERRED EMBODIMENTS

The following description includes a best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

As indicated earlier, the present invention relates to a cardiac stimulation device capable of performing reliable capture verification by detecting a conducted depolarization in a chamber opposite the chamber being stimulated. The methods of the present invention may be implemented in numerous cardiac stimulation devices possessing at least one stimulation and sensing electrode in a right-side chamber and one stimulation and sensing electrode in the opposing left-side chamber, or vice versa. A preferred embodiment of an implantable cardiac stimulation device will be described in conjunction with FIGS. 1 and 2. Moreover, while the invention is described in detail below in connection with the right and left atrium, it will be understood that the invention also applies to conducted depolarization from one ventricle to the other, as is also described below.

Figure 1:
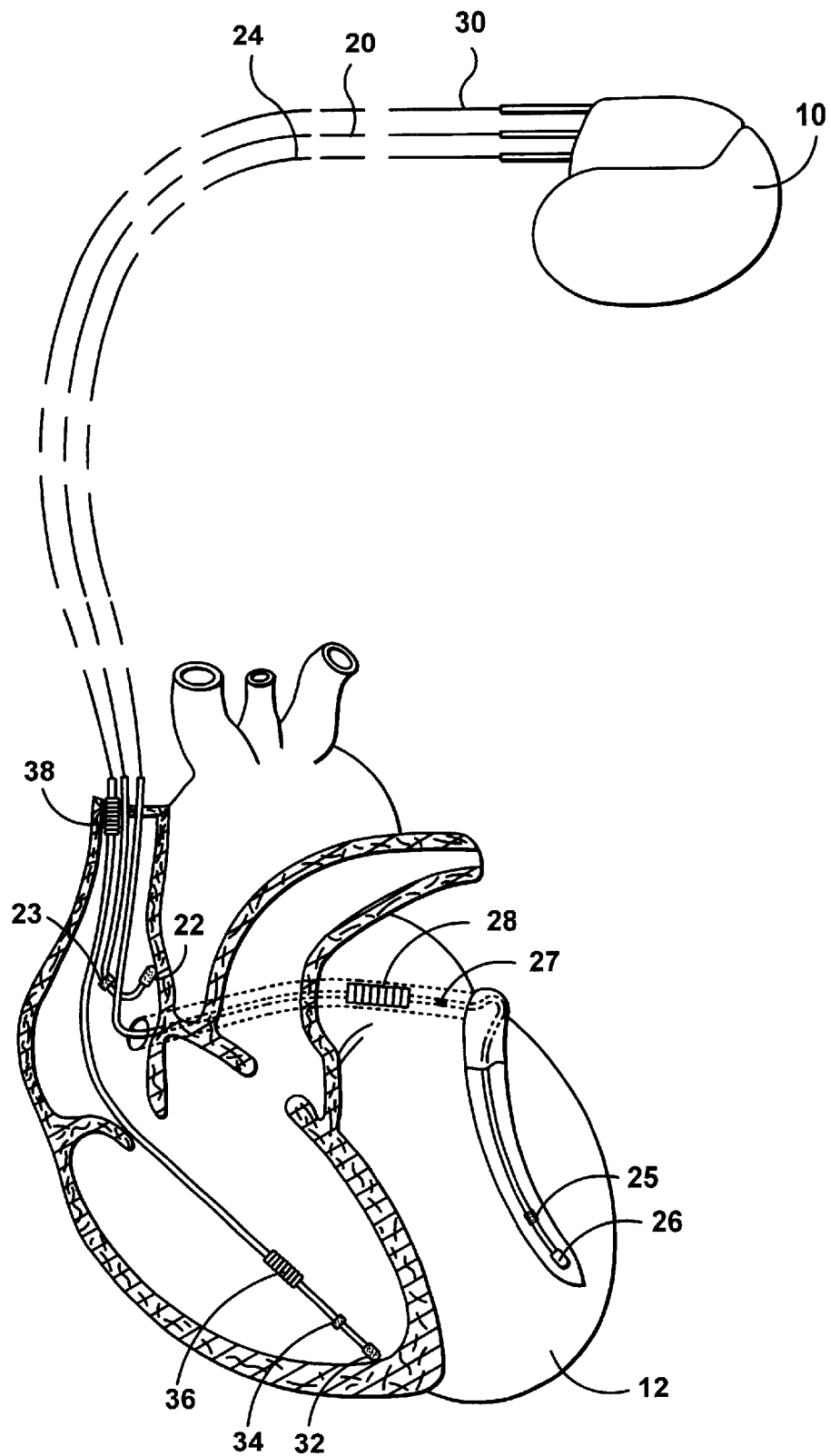
FIG. 1 is a simplified, partly cutaway view of an implantable multi-chamber stimulation device of the present invention, shown in electrical communication with at least three leads implanted into a patient's heart for delivering multi-chamber stimulation and shock therapy.

FIG. 1 illustrates a stimulation device 10 in electrical communication with a patient's heart 12 by way of three leads 20, 24 and 30 suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage. The right atrial lead 20 may also have a right atrial ring electrode 23 to allow bipolar stimulation or sensing in combination with the right atrial tip electrode 22.

To sense left atrial and ventricular cardiac signals and to provide left-chamber stimulation therapy, the stimulation device 10 is coupled to a "coronary sinus" lead 24 designed for placement in the "coronary sinus region" via the coronary sinus os so as to place a distal electrode adjacent to the left ventricle and additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, the coronary sinus lead 24 is designed to receive atrial and ventricular cardiac signals and to deliver: left ventricular pacing therapy using at least a left ventricular tip electrode 26, left atrial pacing therapy using at least a left atrial ring electrode 27, and shocking therapy using at least a left atrial coil electrode 28. In an alternative embodiment, the coronary sinus lead 24 may also include a left ventricular ring electrode 25.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode 36 will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 2:
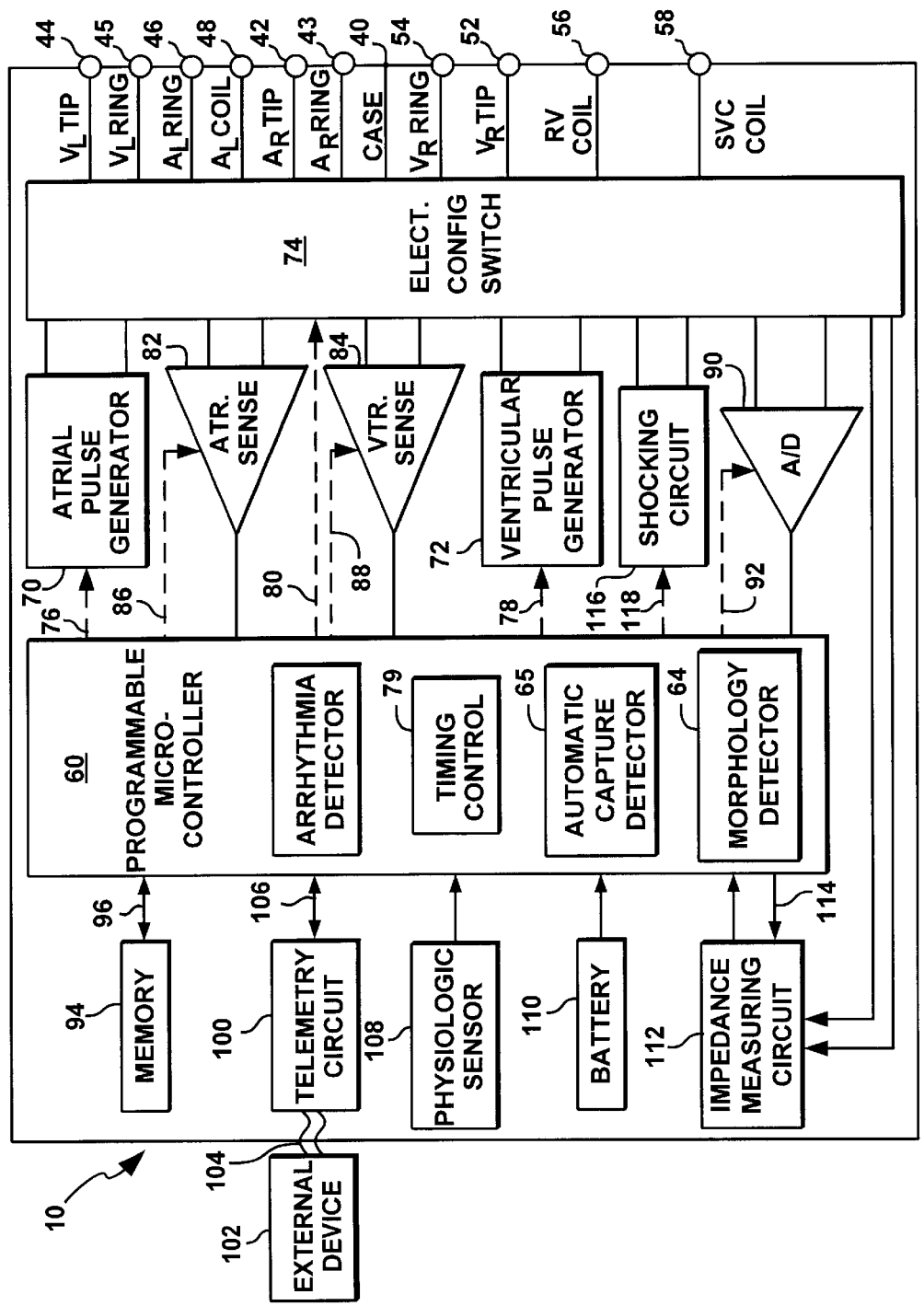
FIG. 2 is a functional block diagram of the multi-chamber implantable stimulation device of FIG. 1, illustrating the basic elements that provide cardioversion, defibrillation and/or pacing stimulation in four chambers of the heart.

FIG. 2 illustrates a simplified block diagram of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and/or pacing stimulation.

The stimulation device 10 includes a housing 40 which is often referred to as "can", "case" or "case electrode", and which may be programmably selected to act as the return electrode for all "unipolar" modes. The housing 40 may further be used as a return electrode alone or in combination with one or more of the coil electrodes 28, 36, or 38, for shocking purposes. The stimulation device 10 further includes a connector having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal 42 adapted for connection to the atrial ($A_R$) tip electrode 22. The connector may also include a right atrial ring terminal (AR RING) 43 for connection to the atrial ring electrode 23, and a left ventricular ring (VL RING) 45 for connection to the left ventricular ring electrode 25.

To achieve left chamber sensing, pacing and/or shocking, the connector includes at least a left ventricular ($V_L$) tip terminal 44, a left atrial ($A_L$) ring terminal 46, and a left atrial ($A_L$)shocking terminal (coil) 48, which are adapted for connection to the left ventricular tip electrode 26, the left atrial tip electrode 27, and the left atrial coil electrode 28, respectively.

To support right chamber sensing, pacing and/or shocking, the connector further includes a right ventricular ($V_R$) tip terminal 52, a right ventricular ($V_R$) ring terminal 54, a right ventricular (RV) shocking terminal (coil) 56, and an SVC shocking terminal (coil) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 that controls the various modes of stimulation therapy. The microcontroller 60 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. Any suitable microcontroller 60 may be used that carries out the functions described herein.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via a switch bank 74. It is understood that in order to provide stimulation therapy in each of the four chambers of the heart, the atrial pulse generator 70 and the ventricular pulse generator 72 may include dedicated, independent pulse generators, multiplexed pulse generators, or shared pulse generators. The atrial pulse generator 70 and the ventricular pulse generator 72 are controlled by the microcontroller 60 via appropriate control signals 76 and 78, respectively, to trigger or inhibit the stimulation pulses.

The microcontroller 60 further includes timing control circuitry 79 which is used to control the timing of such stimulation pulses (e.g. pacing rate, atrio-ventricular (AV) delay, atrial interconduction (A-A) delay, or ventricular interconduction (V-V) delay, etc.), as well as to keep track of the timing of refractory periods, PVARP intervals, noise detection windows, evoked response windows, alert intervals, marker channel timing, etc.

The switch bank 74 includes a plurality of switches for connecting the desired electrodes to the appropriate I/O circuits, thereby providing complete electrode programmability. Accordingly, the switch bank 74, in response to a control signal 80 from the microcontroller 60, determines the polarity of the stimulation pulses (e.g. unipolar, bipolar, cross-chamber, etc.) by selectively closing the appropriate combination of switches.

Atrial sensing circuits 82 and ventricular sensing circuits 84 may also be selectively coupled to the right atrial lead 20, coronary sinus lead 24, and the right ventricular lead 30, through the switch bank 74, for detecting the presence of cardiac activity in each of the four chambers of the heart. Accordingly, the atrial and ventricular sensing circuits 82 and 84 may include dedicated sense amplifiers, multiplexed amplifiers, or shared amplifiers. The switch bank 74 determines the "sensing polarity" of the cardiac signal by selectively closing the appropriate switches. In this way, the clinician may program the sensing polarity independent of the stimulation polarity.

In accordance with the present invention, sensing during the capture verification methods to be described herein will be performed in the opposing atrial chamber. Thus, switch bank 74 will selectively close the appropriate switches such that during an atrial capture detection window, sensing electrodes positioned in the atrial chamber opposite that being stimulated are connected to the appropriate atrial sensing circuits 82.

Each of the atrial sensing circuit 82 or the ventricular sensing circuit 84 preferably employs one or more low power, precision amplifiers with programmable gain and/or automatic gain control, bandpass filtering, and a threshold detection circuit, to selectively sense the cardiac signal of interest. The automatic gain control enables the stimulation device 10 to deal effectively with the difficult problem of sensing the low amplitude signal characteristics of atrial or ventricular fibrillation.

The outputs of the atrial and ventricular sensing circuits 82 and 84 are connected to the microcontroller 60 for triggering or inhibiting the atrial and ventricular pulse generators 70 and 72, respectively, in a demand fashion, in response to the absence or presence of cardiac activity, respectively, in the appropriate chambers of the heart. The atrial and ventricular sensing circuits 82 and 84, in turn, receive control signals over signal lines 86 and 88 from the microcontroller 60, for controlling the gain, threshold, polarization charge removal circuitry, and the timing of any blocking circuitry coupled to the inputs of the atrial and ventricular sensing circuits 82 and 84. In accordance with the present invention, timing signals associated with the onset and duration of an atrial capture detection window may be received over signal lines 86 and 88.

For arrhythmia detection, the stimulation device 10 utilizes the atrial and ventricular sensing circuits 82 and 84 to sense cardiac signals, for determining whether a rhythm is physiologic or pathologic. As used herein "sensing" is reserved for the noting of an electrical signal, and "detection" is the processing of these sensed signals and noting the presence of an arrhythmia. The timing intervals between sensed events (e.g. P-waves, R-waves, and depolarization signals associated with fibrillation which are sometimes referred to as "F-waves" or "Fib-waves") are then classified by the microcontroller 60 by comparing them to a predefined rate zone limit (e.g. bradycardia, normal, low rate VT, high rate VT, and fibrillation rate zones) and various other characteristics (e.g. sudden onset, stability, physiologic sensors, and morphology, etc.) in order to determine the type of remedial therapy that is needed (e.g. bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram signals, convert the raw analog data into digital signals, and store the digital signals for later processing and/or telemetric transmission to an external device 102. The data acquisition system 90 is coupled to the right atrial lead 20, the coronary sinus lead 24, and the right ventricular lead 30 through the switch bank 74 to sample cardiac signals across any pair of desired electrodes.

The data acquisition system 90 may be coupled to the microcontroller 60 or another detection circuitry, for detecting an evoked response from the heart 12 in response to an applied stimulus, thereby aiding in the detection of "capture" as will be described in detail in conjunction with FIG. 3. Capture detection may involve differentiation, integration, or other morphological analyses of the sampled signals, or a sensed signal above a predetermined sensing threshold. Morphology detector 64 of microcontroller 60 may be used for comparing a sensed signal with morphological characteristics of a depolarization signal. For a more detailed description of the implementation of capture detection circuitry and algorithms refer, for example, to U.S. Pat. No. 5,350,410 to Kleks et al.

The microcontroller 60 could also include an automatic capture detector 65 that enables capture detection by triggering the atrial pulse generator 70 to generate a stimulation pulse, starting the atrial capture detection window using the timing circuitry within the microcontroller 60, and enabling the data acquisition system 90 via control signal 92 to sample the cardiac signal that falls in the atrial capture detection window and, based on the amplitude of the sampled cardiac signal, determines if capture has occurred.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

Advantageously, the operating parameters of the stimulation device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller 60by a control signal 106. The telemetry circuit 100 advantageously allows intracardiac electrograms and status information relating to the operation of the stimulation device 10 (as contained in the microcontroller 60 or memory 94) to be sent to the external device 102 through the established communication link 104.

In one embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g. detecting sleep and wake states). Accordingly, the microcontroller 60 responds by adjusting the various pacing parameters (such as rate, AV Delay, V-V Delay, etc.) at which the atrial and ventricular pulse generators 70 and 72 generate stimulation pulses.

The stimulation device 10 additionally includes a power source such as a battery 110 that provides operating power to all the circuits shown in FIG. 2. For the stimulation device 10, which employs shocking therapy, the battery 110 must be capable of operating at low current drains for long periods of time, and also be capable of providing high-current pulses (for capacitor charging) when the patient requires a shock pulse. The battery 110 must preferably have a predictable discharge characteristic so that elective replacement time can be detected.

As further shown in FIG. 2, the stimulation device 10 is shown as having an impedance measuring circuit 112 which is enabled by the microcontroller 60 by a control signal 114.

If it is a function of the stimulation device 10 to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 Joules), moderate (0.5–10 Joules), or high (11 to 40 Joules) energy, as controlled by the microcontroller 60. Such shocking pulses are applied to the patient's heart through at least two shocking electrodes, and as shown in this embodiment, selected from the left atrial coil electrode 28, the RV coil electrode 36, and/or the SVC coil electrode 38 (FIG. 1). As noted above, the housing 40 may act as an active electrode in combination with the RV electrode 36, or as part of a split electrical vector using the SVC coil electrode 38 or the left atrial coil electrode 28 (i.e., using the RV electrode as common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 540 Joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Figure 3:
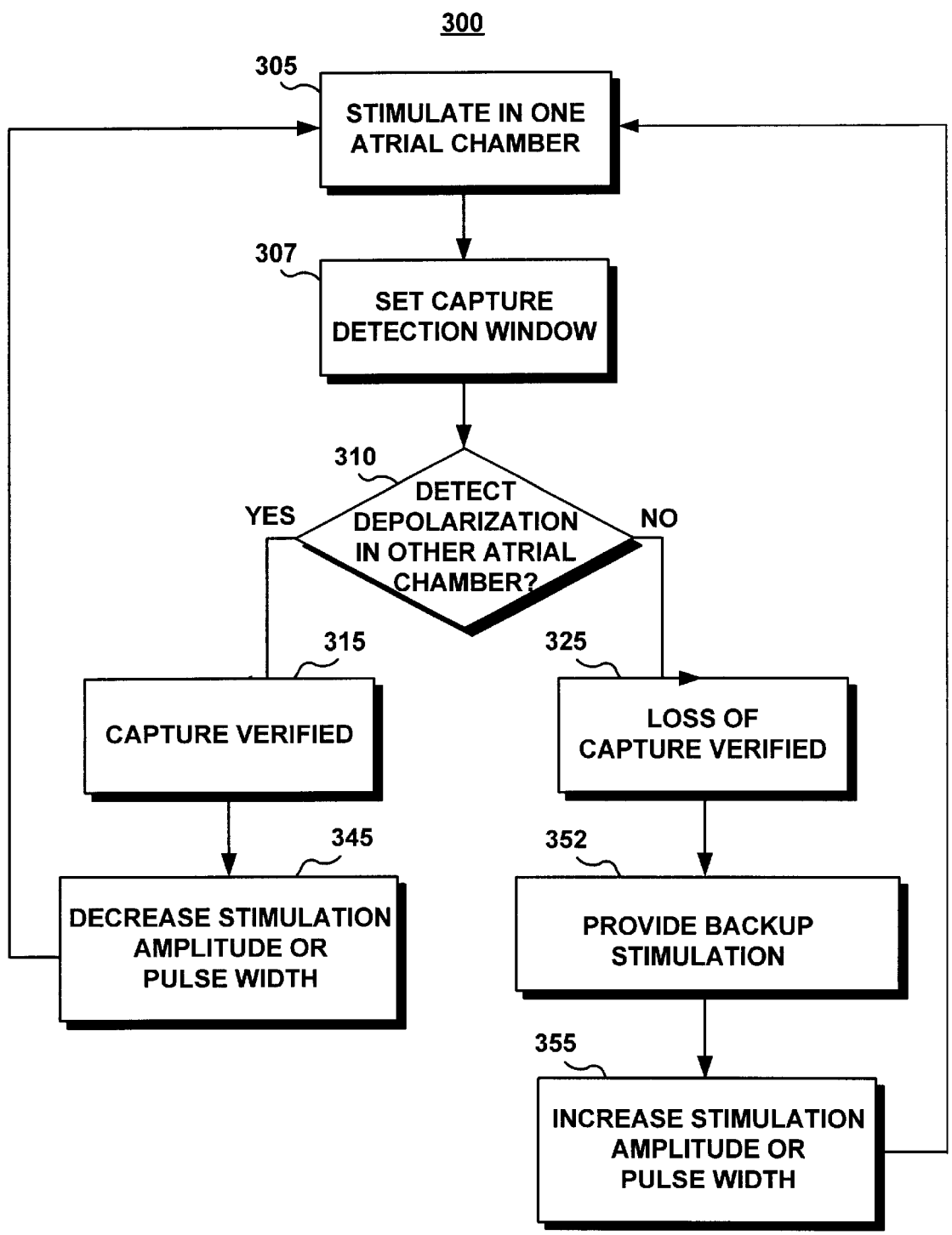
FIG. 3 is a functional flow chart illustrating the operation of an exemplary embodiment of the stimulation device of FIGS. 1 and 2, for performing capture verification according to the present invention.

In FIG. 3, a flow chart is shown describing an overview of the operation and features implemented in one embodiment of the stimulation device 10 for performing capture verification. In this flow chart, the various algorithmic steps are summarized in individual "blocks". Such blocks describe specific actions or decisions that must be made or carried out as the algorithm proceeds. Where a microcontroller (or equivalent) is employed, the flow chart provides the basis for a "control program" that may be used by such a microcontroller (or equivalent) to effectuate the desired control of the stimulation device. Those skilled in the art may readily write such a control program based on the flow chart and other descriptions presented herein.

At step 305 of method 300, a stimulation pulse is delivered to an atrial chamber, either right or left, of the heart. The method 300 applies to either atrial chamber, and thus method 300 will be described in one atrial chamber with capture detected in the opposite atrial chamber. For stimulation in the atrial chamber, atrial pulse generator 70 delivers a stimulation pulse according to timing control 79 of microprocessor 60.

At step 310, the intracardiac electrogram signal is sensed in the opposing atrial chamber during the atrial capture detection window. Thus, if stimulation were delivered in the right atrial chamber, sensing at step 310 is performed in the left atrial chamber. Similarly, if stimulation were delivered in the left atrial chamber, sensing at step 310 is performed in the right atrial chamber.

The intracardiac electrogram signal is received by the appropriate atrial sensing circuit 82. Alternatively or additionally, the sensed intracardiac electrogram signal is received by the A/D converter 90 where it may be sampled and digitized.

The atrial capture detection window may begin at a predefined delay (i.e., approximately 10 msec.) following the delivery of the stimulation pulse. Normally, conduction from one atrial chamber to the opposing atrial chamber occurs within approximately 10 msec to 20 msec. Preferably, the atrial capture detection window extends approximately 10 msec to 50 msec beyond the expected inter-chamber conduction time. The timing of the atrial capture detection window, its onset and duration, are predetermined. Alternatively, they can be programmable so that it may be tailored to individual patient conditions to account for variations in intra-chamber and inter-chamber conduction times.

A conducted depolarization may be detected by standard techniques used in known capture verification methods (step 307). For example, a depolarization sensing threshold may be set such that if the received signal exceeds the depolarization threshold, a conducted depolarization is verified. Other techniques may determine a slope, integral, or other characteristic of the received signal that may be compared to a predefined depolarization threshold value.

Figure 4:
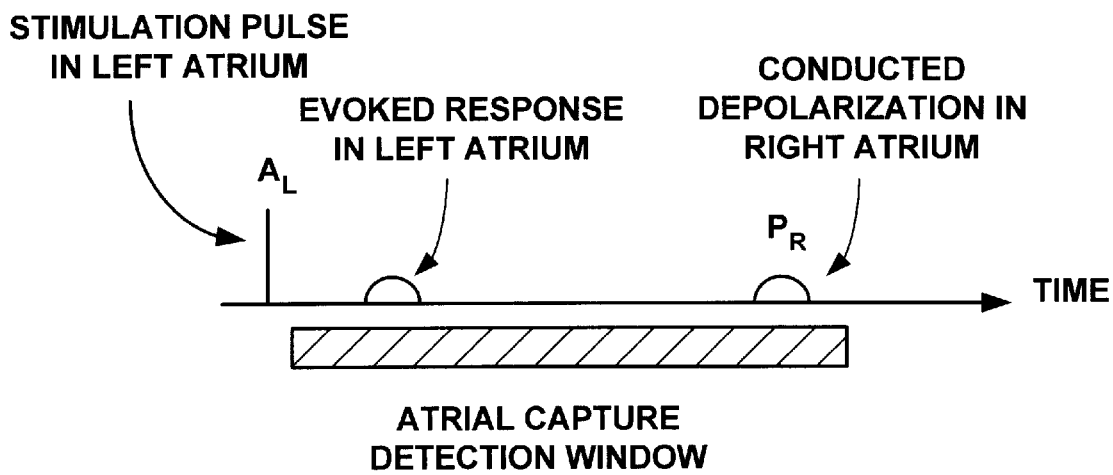
FIG. 4 is a timing diagram depicting a sequence of signals occurring during the execution of the method of FIG. 3 for detecting a conducted depolarization in the form of a signal conducted along an inter-atrial path to a non-stimulated atrial chamber.

Capture verification method determines at decision step 310 if a conducted depolarization is detected in the opposite or non-stimulated atrial chamber, within the atrial capture detection window that follows an atrial stimulation. FIG. 4 illustrates an atrial stimulation ($A_L$) in the left atrium.

If a conducted depolarization in the opposite, non-stimulated atrium (i.e., right atrium in this example) is detected, then capture of the stimulated atrial chamber is verified at step 315.

FIG. 4 illustrates as an example, the conducted depolarization ($P_R$) Of the non-stimulated atrial chamber (e.g., the right atrium), in response to the atrial stimulation ($A_L$) in the left atrium that has propagated along an inter-atrial path to the non-stimulated atrial. It will be apparent to those skilled in the art that in another embodiment of the invention, the atrial stimulation can occur in the right atrium, and that sensing of the conducted depolarization occurs in the left atrium. As shown in FIG. 4, the capture detection window begins some amount of time after the stimulation pulse $A_L$) is delivered to the left atrium, to prevent the device from sensing the stimulation pulse in the non-stimulated chamber.

When capture is verified at step 315, the stimulation amplitude or pulse width is decremented at step 345, and method 300 returns to step 305 and awaits for the next stimulation pulse delivery. In this way, beat-by-beat capture verification can be performed. In alternative embodiments, the method 300 may be performed less frequently, for example after a given number of stimulation cycles, once per minute, hourly, daily, etc.

Returning to decision step 310, if a depolarization signal is not detected, loss of capture is verified at step 325, and backup stimulation is provided at step 352. If a number of consecutive losses, such as 2 losses of capture occur, the stimulation amplitude or pulse width may be increased at step 355, whereupon method 300 returns to step 305.

While the invention has been described primarily in connection with the atria of the heart, it will be apparent to those skilled in the art that the invention has utility in connection with the ventricles as well. In that embodiment, stimulation device 10 is coupled to the coronary sinus lead 24, which is designed to place one or more electrodes through the coronary sinus region and down through one of the veins on the outer surface of the left ventricle to be adjacent to the left ventricle for stimulating the left ventricle and/or for sensing electrical activity of that ventricle. Examples of suitable veins include the great cardiac vein, left marginal vein, left posterior ventricular vein, middle cardiac vein, and/or small cardiac vein or any other cardiac vein accessible by the coronary sinus.

In addition, in this alternative embodiment stimulation device 10 also includes the implantable right ventricular lead 30 to receive cardiac signals and deliver stimulation in the form of pacing and shock therapy to the right ventricle.

This alternative embodiment operates in much the same manner as the embodiment described above in connection with the atria. A stimulation pulse is delivered to one of the ventricles, and a capture detection window is defined, which begins some period of time after delivery of the stimulation pulse and lasts for a preset, programmable duration. If depolarization is sensed in the non-stimulated ventricle during the capture detection window, then it is determined that the opposite ventricle successfully depolarized in response to the applied stimulation pulse.

Thus, a method and apparatus have been described which allow reliable capture verification during cardiac stimulation by detecting a cross-chamber conducted depolarization. The methods of the present invention advantageously avoid problems associated with lead polarization by sensing cardiac activity away from the site of stimulation. The cardiac stimulation device performance is improved by allowing capture verification regimes, such as automatic capture, to be executed more reliably. While the invention has been described according to specific embodiments and applications thereof, numerous modifications and variations could be made thereto by those skilled in the art.

What is claimed:

1. A method of verifying capture of a first chamber for use in a cardiac stimulation device, the method comprising:
   delivering a stimulation pulse to a first chamber;
   setting a capture detection window following the deliver of the stimulation pulse; and
   detecting, within a coronary sinus region, a depolarization signal of a second chamber during the capture detection window for verifying capture of the first chamber;
   wherein the step of setting the capture detection window includes:
      starting the capture detection window after a predetermined delay following the delivery of the stimulation pulse; and
      extending the capture detection window beyond an expected inter-chamber conduction time required for an evoked depolarization signal at the first chamber to travel to the second chamber.

2. The method of claim 1, wherein the step of extending the capture detection window includes setting a duration of the capture detection window for approximately 20 msec to 50 msec, beyond the inter-chamber expected conduction time.

3. A method of verifying capture of a first chamber for use in a cardiac stimulation device, the method comprising:
   delivering a stimulation pulse to a first chamber;
   setting a capture detection window following the delivery of the stimulation pulse; and
   detecting, within a coronary sinus region, a depolarization signal of a second chamber during the capture detection window for verifying capture of the first chamber; and
   verifying loss of capture of the first chamber if a depolarization signal of the second chamber is not detected.

4. The method of claim 3, wherein delivering a stimulation pulse comprises delivering a stimulation pulse to a first atrial chamber, and wherein detecting a depolarization signal comprises detecting a depolarization signal of a second atrial chamber.

5. The method of claim 4, further including the step of confirming capture of the first atrial chamber when capture is verified.

6. The method of claim 4, further including the step of increasing the stimulation pulse energy at the first atrial chamber if loss of capture is verified.

7. The method of claim 4, further including the step of decreasing the stimulation pulse at the first atrial chamber if capture is verified.

8. The method of claim 3, wherein delivering a stimulation pulse comprises delivering a stimulation pulse to a first ventricular chamber, and wherein detecting a depolarization signal comprises detecting a depolarization signal of a second ventricular chamber.

9. A cardiac stimulation device for verifying capture of a first chamber, comprising:
   a pulse generator that selectively generates stimulation energy;
   a lead, connected to the pulse generator, that delivers the stimulation energy to the first chamber;
   a timing circuit that sets a capture detection window in response to the delivery of the stimulation pulse; and a sensor that is adapted to be placed in a coronary sinus region and that is operative to detect a depolarization signal of a second chamber during the capture detection to verify capture of the first chamber;

wherein the timing circuit starts the capture detection window at a predetermined delay following the delivery of the stimulation energy.

10. The device of claim 9, wherein the capture detection window extends beyond an inter-chamber expected conduction time required for an evoked depolarization signal at the first chamber to travel to the second chamber.

11. The device of claim 10, wherein the capture detection window extends for approximately 10 msec to 20 msec beyond the inter-chamber expected conduction time.

12. A cardiac stimulation device for verifying capture of a first chamber, comprising:

a pulse generator that selectively generates stimulation energy;

a lead, connected to the pulse generator, that delivers the stimulation energy to the first chamber;

a timing circuit that sets a capture detection window in response to the delivery of the stimulation pulse; and a sensor that is adapted to be placed in a coronary sinus region, the sensor operative to detect a depolarization signal of a second chamber during the capture detection to verify capture of the first chamber, and the sensor to verify loss of capture of the first chamber if a depolarization signal of the second chamber is not detected.

13. The device of claim 12, wherein the lead is designed to deliver a stimulation pulse to a first atrial chamber, and wherein the sensor is designed to sense depolarization of a second atrial chamber.

14. The device of claim 12, wherein the lead is designed to deliver a stimulation pulse to a first ventricular chamber, and wherein the sensor is designed to sense depolarization of a second ventricular chamber.

15. A cardiac stimulation device for verifying capture of a first chamber, comprising:

means for delivering stimulation energy to the first chamber:

means for setting a capture detection window following the delivery of stimulation energy to the first chamber: and means for detecting depolarization of a second chamber in a coronary sinus region, during the capture detection window, to verify capture of the first chamber;

wherein the capture detection window extends for approximately 10 msec to 20 msec beyond the inter-chamber expected conduction time.

16. A cardiac stimulation device for verifying capture of a first chamber, comprising:

means for delivering stimulation energy to the first chamber:

means for setting a capture detection window following the delivery of stimulation enemy to the first chamber; and means for detecting depolarization of a second chamber in a coronary sinus region, during the capture detection window, to verify capture of the first chamber;

wherein the means for detecting the conducted depolarization at the second chamber in response to the stimulation of the first chamber includes a unipolar electrode configuration.

17. A cardiac stimulation device for verifying capture of a first chamber, comprising:

means for delivering stimulation energy to the first chamber;

means for setting a capture detection window following the delivery of stimulation energy to the first chamber; and means for detecting depolarization of a second chamber in a coronary sinus region, during the capture detection window, to verify capture of the first chamber;

wherein the verifying means verifies capture of the first chamber if a conducted depolarization is detected; and wherein the verifying means verifies loss of capture of the first chamber if the conducted depolarization is not detected.

18. The device of claim 17, further including means for comparing a morphology of an intracardiac electrogram signal to a morphology of the depolarization template to confirm capture.

19. The device of claim 17, wherein the conducted depolarization includes a conducted depolarization of the second chamber along an inter-chamber path in response to the stimulation of the first chamber.

20. The device of claim 17, wherein the means for detecting the conducted depolarization at the second chamber in response to the stimulation of the first chamber includes a bipolar electrode configuration.

21. The device of claim 17, wherein the means for delivering stimulation energy comprises means for delivering a stimulation pulse to a first atrial chamber, and wherein the means for detecting depolarization comprises means for detecting depolarization of a second atrial chamber.

22. The device of claim 17, wherein the means for delivering stimulation energy comprises means for delivering a stimulation pulse to a first ventricular chamber, and wherein the means for detecting depolarization comprises means for detecting depolarization of a second ventricular chamber.

* * * * *